(12) United States Patent
Coleman

(10) Patent No.: US 6,308,713 B1
(45) Date of Patent: Oct. 30, 2001

(54) HEEL PROTECTION DEVICE

(76) Inventor: Graham G. Coleman, 14 The Fairway, Flackwell Heath, High Wycombe, Bucks HP10 9NF (GB)

( * ) Notice: Subject to any disclaimer, the term of this patent is extended or adjusted under 35 U.S.C. 154(b) by 0 days.

(21) Appl. No.: 09/633,572

(22) Filed: Aug. 4, 2000

(51) Int. Cl.⁷ .................................................. A61F 5/37
(52) U.S. Cl. .......................................... 128/882; 128/892
(58) Field of Search .................................. 128/846, 869, 128/882, 892; 602/23, 5, 27, 646, 647, 648

(56) References Cited

U.S. PATENT DOCUMENTS

| | | |
|---|---|---|
| D. 261,821 | 11/1981 | Hubbard et al. . |
| D. 364,009 | 11/1995 | Engdahl . |
| 1,562,454 | 11/1925 | Jenkins . |
| 2,592,739 | 4/1952 | Richardson . |
| 3,216,417 * | 11/1965 | Posey ..................................... 128/892 |
| 3,670,725 | 6/1972 | Gaylord, Jr. . |
| 3,693,619 | 9/1972 | Williams . |
| 3,937,218 | 2/1976 | Gaylord, Jr. . |
| 4,186,738 * | 2/1980 | Schleicher ............................. 128/802 |
| 4,471,770 * | 9/1984 | Pompa ................................... 128/892 |
| 5,083,557 * | 1/1992 | Lennon ................................. 128/882 |
| 5,449,339 * | 9/1995 | Drennan ................................ 128/882 |
| 6,194,629 * | 2/2001 | Bernhard ............................... 128/882 |

\* cited by examiner

*Primary Examiner*—Michael A. Brown

(57) ABSTRACT

A heel protection device for protecting a portion of the heel of a user's foot from developing sores from prolonged contact with bedding during a period of bedrest. The heel protection device includes a cap member for receiving the heel portion of the user's foot, and a securing strap assembly for securing the cap member on the heel portion of the user's foot. The cap member comprises a base portion for positioning adjacent to a sole of the user's foot, a back portion mounted on the base portion at a rearward location of the base portion that extends substantially perpendicular to the base portion, and a pair of laterally spaced side portions mounted on lateral side locations of the base portion and the back portion, with the side portions being oriented substantially perpendicularly to the base portion.

1 Claim, 2 Drawing Sheets

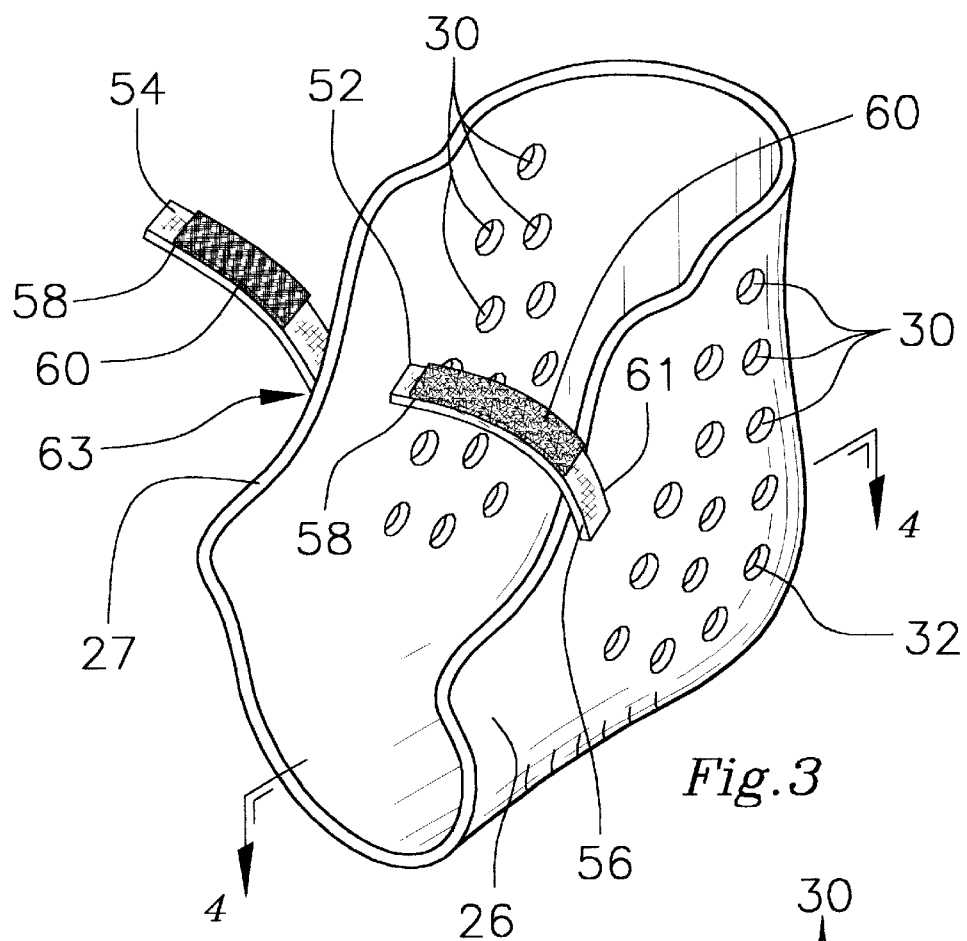
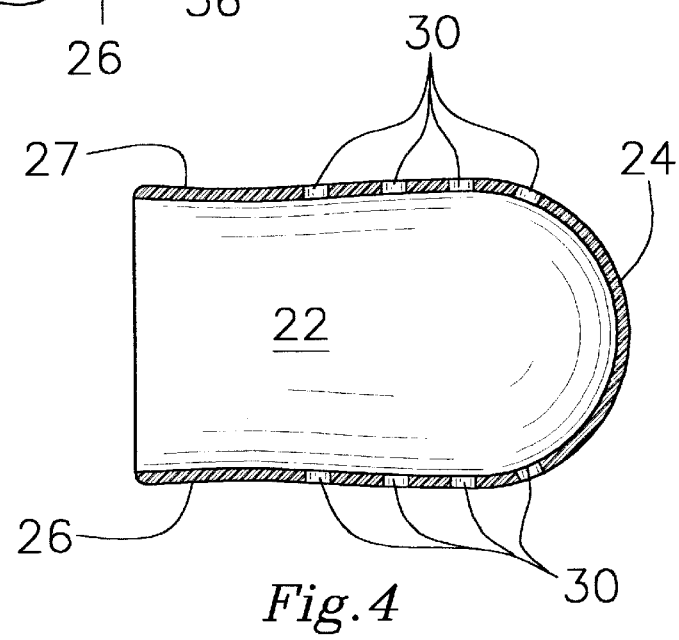

HEEL PROTECTION DEVICE

BACKGROUND OF THE INVENTION

1. Field of the Invention

The present invention relates to heel protection device and more particularly pertains to a new heel protection device for protecting a portion of the heel of a user's foot from developing sores from prolonged contact with bedding during a period of bedrest.

2. Description of the Prior Art

The use of a heel protection device is known in the prior art. More specifically, heel protection devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 3,937,218; 1,562,454; 2,592,739; 3,693,619; 3,670,725; and Des. 261,821 and Des. 364,009.

While these devices fulfill their respective, particular objectives and requirements, the aforementioned patents do not disclose a new heel protection device. The inventive device includes a cap member for receiving the heel portion of the user's foot, and a securing strap assembly for securing the cap member on the heel portion of the user's foot. The cap member comprises a base portion for positioning adjacent to a sole of the user's foot, a back portion mounted on the base portion at a rearward location of the base portion that extends substantially perpendicular to the base portion, and a pair of laterally spaced side portions mounted on lateral side locations of the base portion and the back portion, with the side portions being oriented substantially perpendicularly to the base portion.

In these respects, the heel protection device according to the present invention substantially departs from the conventional concepts and designs of the prior art, and in so doing provides an apparatus primarily developed for the purpose of protecting a portion of the heel of a user's foot from developing sores from prolonged contact with bedding during a period of bedrest.

SUMMARY OF THE INVENTION

In view of the foregoing disadvantages inherent in the known types of heel protection device now present in the prior art, the present invention provides a new heel protection device construction wherein the same can be utilized for protecting a portion of the heel of a user's foot from developing sores from prolonged contact with bedding during a period of bedrest.

The general purpose of the present invention, which will be described subsequently in greater detail, is to provide a new heel protection device apparatus which has many of the advantages of the heel protection device mentioned heretofore and many novel features that result in a new heel protection device which is not anticipated, rendered obvious, suggested, or even implied by any of the prior art heel protection device, either alone or in any combination thereof.

To attain this, the present invention generally comprises a cap member for receiving the heel portion of the user's foot, and a securing strap assembly for securing the cap member on the heel portion of the user's foot. The cap member comprises a base portion for positioning adjacent to a sole of the user's foot, a back portion mounted on the base portion at a rearward location of the base portion that extends substantially perpendicular to the base portion, and a pair of laterally spaced side portions mounted on lateral side locations of the base portion and the back portion, with the side portions being oriented substantially perpendicularly to the base portion.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new heel protection device apparatus and method which has many of the advantages of the heel protection device mentioned heretofore and many novel features that result in a new heel protection device which is not anticipated, rendered obvious, suggested, or even implied by any of the prior art heel protection device, either alone or in any combination thereof.

It is another object of the present invention to provide a new heel protection device that may be easily and efficiently manufactured and marketed.

It is a further object of the present invention to provide a new heel protection device that is of a durable and reliable construction.

An even further object of the present invention is to provide a new heel protection device which is susceptible of a low cost of manufacture with regard to both materials and labor, and which accordingly is then susceptible of low prices of sale to the consuming public, thereby making such heel protection devices economically available to the buying public.

Still yet another object of the present invention is to provide a new heel protection device which provides in the apparatuses and methods of the prior art some of the advantages thereof, while simultaneously overcoming some of the disadvantages normally associated therewith.

Still another object of the present invention is to provide a new heel protection device for protecting a portion of the heel of a user's foot from developing sores from prolonged contact with bedding during a period of bedrest.

Yet another object of the present invention is to provide a new heel protection device that includes a cap member for receiving the heel portion of the user's foot, and a securing strap assembly for securing the cap member on the heel portion of the user's foot. The cap member comprises a base portion for positioning adjacent to a sole of the user's foot, a back portion mounted on the base portion at a rearward location of the base portion that extends substantially perpendicular to the base portion, and a pair of laterally spaced side portions mounted on lateral side locations of the base portion and the back portion, with the side portions being oriented substantially perpendicularly to the base portion.

Still yet another object of the present invention is to provide a new heel protection device that permits a user's foot to receive ventilation while protecting the heel from developing bed sores during a prolonged bed rest due to the eliminated friction.

Even still another object of the present invention is to provide a new heel protection device that provides the user with the option of also creating friction between the gripping strips and another surface if necessary, for example, such as when a user placed her feet flat on a surface.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic side view of the present invention.

FIG. 4 is a schematic cross section view taken along line 4—4 of FIG. 3 of the present invention.

DESCRIPTION OF THE PREFERRED EMBODIMENT

Figure 1:
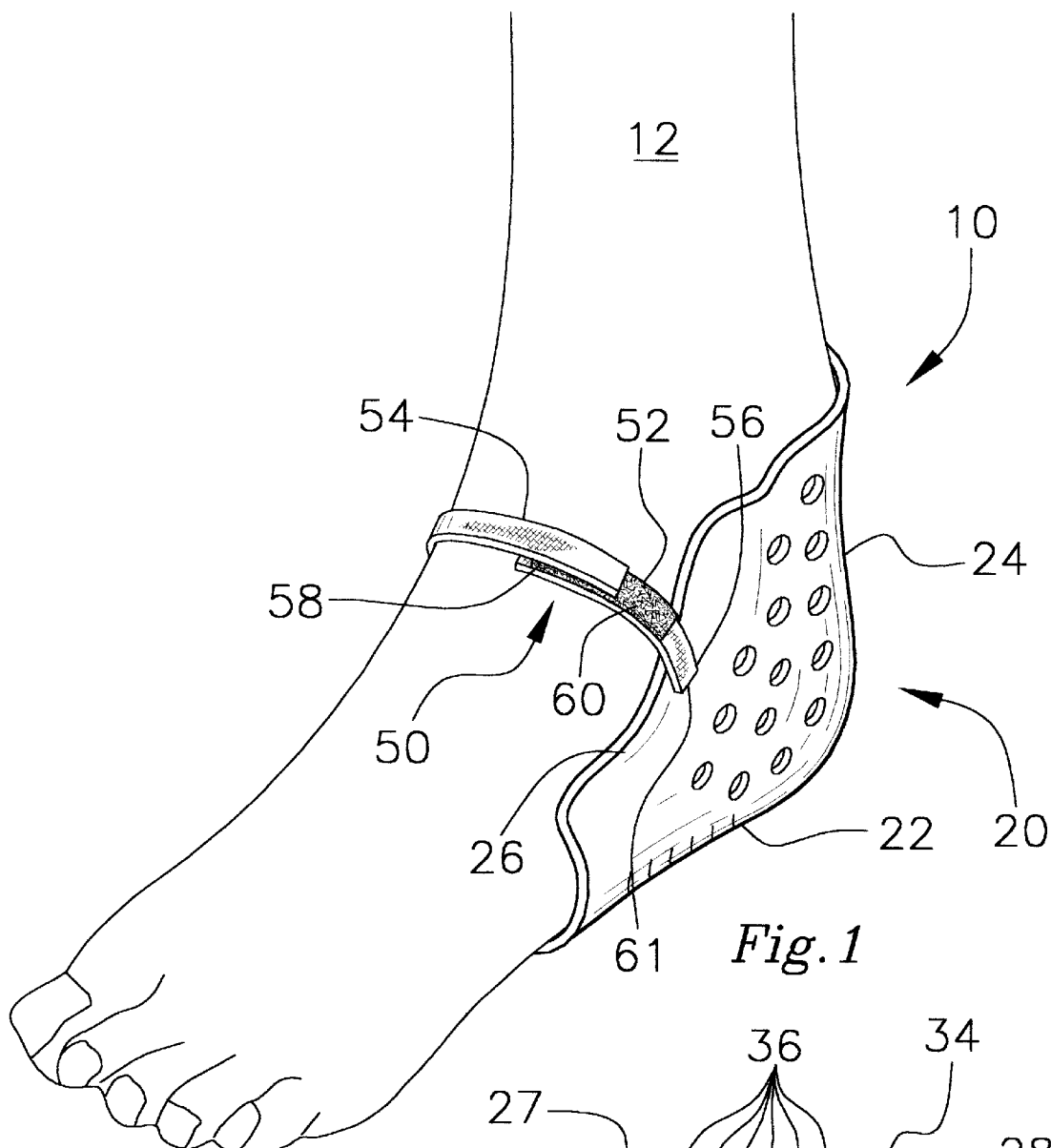
FIG. 1 is a schematic perspective view of a new heel protection device according to the present invention.
Figure 2:
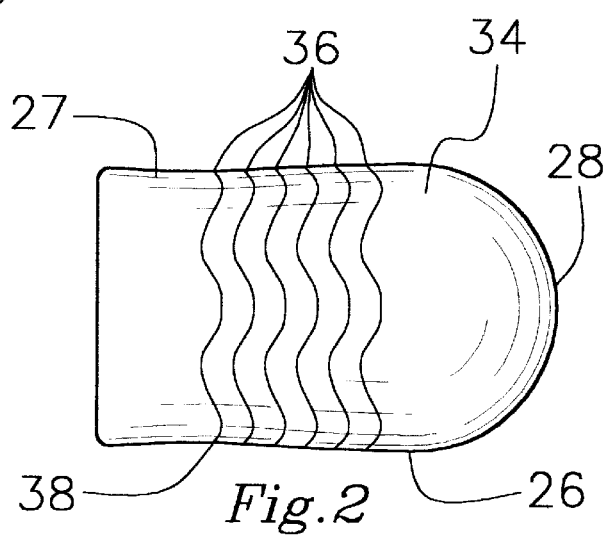
FIG. 2 is a schematic bottom view of the present invention.

With reference now to the drawings, and in particular to FIGS. 1 through 4 thereof, a new heel protection device embodying the principles and concepts of the present invention and generally designated by the reference numeral 10 will be described.

As best illustrated in FIGS. 1 through 4, the heel protection device 10 generally comprises a cap member 20 to receive the heel portion of the user's foot 12. The cap member 20 includes a base portion 22 for positioning adjacent to a sole of the user's foot 12. A back portion 24 is mounted on the base portion 22 at a rearward location of the base portion 22 and extends substantially perpendicular to the base portion 22.

A pair of laterally spaced side portions 26 and 27 are mounted on lateral side locations of the base portion 22 and the back portion 24. Each of the side portions 26 and 27 is oriented substantially perpendicularly to the base portion 22. Each side portion 26 and 27 may be generally triangular in shape and substantially planar. The base portion 22 includes an arcuate cross-section in a plane oriented substantially parallel to the back portion 24. The back portion 24 may have an arcuate cross-section in a plane 28 oriented substantially parallel to the base portion 22. The cap member 20 may be formed from a resiliently flexible material.

A securing strap assembly 50 secures the cap member 20 on the heel portion of the user's foot 12. The securing strap assembly 50 includes a first strap section 52 and a second strap section 54. Each of the strap sections 52, 54 includes a first end 56 mounted on each of the side portions 26, 27 of the cap member 20 and a second end 58 with means for connecting each of the second ends 58 together, such as a hook and loop fastener component 60. The hook and loop fastener 60 of one strap section 52 is designed to releasably engage the hook and loop fastener component 60 of the other strap section 54.

In one embodiment of the invention, each of the side portions 26, 27 includes a plurality of ventilation holes 30 formed therein for allowing air flow between the cap member 20 and the user's foot thus providing more comfort for the user's foot 12. Each of the ventilation holes 32 extends through one of the side walls 26, 27.

A plurality of gripping strips 36 is formed on a lower surface 34 of the base portion 22 for permitting the user to create friction between the heel protection device 10 and a surface such as a bed. This allows the user some stability while, for example, trying to move from a reclining to a sitting position or to move the knees into a bent position. Each of the gripping strips 38 may extend from a location adjacent to a first one 61 of the side portions 26 to a location adjacent to a second one 63 of the side portions 26. The strips 38 each preferably have a serpentine shape. The plurality of gripping strips 36 may ideally comprise at least six strips 38.

In use, the heel protection device is placed on the heel portion of the user and secured with the securing strap assembly. The outer surface of the back portion easily slides over bedding surfaces and protects the user's heel from rubbing and concentrated pressure. Optionally, the user may place her feet flat on a surface with the sole of her feet touching a surface and place the bottom portion of the heel protection device in contact with a bedding surface such that the gripping strips create friction between the bedding and the device to give the user leverage to, for example, assist her in pushing her body to an upward position or allowing her legs to be moved to a position where the knees are bent.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A device for protecting a heel portion of a user's foot from developing sores, comprising:

a cap member for receiving the heel portion of the user's foot, the cap member comprising a base portion for positioning adjacent to a sole of the user's foot, a back portion mounted on the base portion at a rearward location of the base portion and extending substantially perpendicular to the base portion, a pair of laterally spaced side portions mounted on lateral side locations of the base portion and the back portion, the side portions being oriented substantially perpendicularly to the base portions, each of the side portions being generally planar, the base portion having an arcuate cross-section in a plane oriented substantially parallel to the back portion, the back portion having an arcuate cross-section in a plane oriented substantially parallel to the base portion, the cap member being formed from a resiliently flexible material;

wherein said cap member has a single foot receiving opening defined by edges on said side portions, said back portion and said base portion such that the foot of the user may be rested in an interior of said cap member for cradling the user's foot.

a securing strap assembly for securing the cap member on the heel portion of the user's foot, the securing strap assembly having a first strap section and a second strap section, each of the strap sections having a first end mounted on a side portion of the cap member, each of the strap sections having a second end with a hook and look fastener component adapted to releasably engage the hook and loop fastener component of the other strap section;

wherein each of the side portions has a plurality of ventilation holes formed therein, each of the ventilation holes extending through one of the side walls; and wherein a plurality of gripping strips are formed on a lower surface of the base portion, each of the gripping strips extending transversely from a location adjacent to a first one of the side portions to a location adjacent to a second one of the side portions, each of the strips having a serpentine shape, the plurality of gripping strips comprising at least six strips.

* * * * *